United States Patent
del Rio et al.

(10) Patent No.: US 10,842,508 B2
(45) Date of Patent: Nov. 24, 2020

(54) DISPOSABLE BURR ATTACHMENT

(71) Applicant: DePuy Synthes Products, Inc., Raynham, MA (US)

(72) Inventors: Eddy H. del Rio, Royal Palm Beach, FL (US); Douglas A. Perry, Palm Beach Gardens, FL (US)

(73) Assignee: DePuy Synthes Products, Inc., Raynham, MA (US)

(*) Notice: Subject to any disclaimer, the term of this patent is extended or adjusted under 35 U.S.C. 154(b) by 71 days.

(21) Appl. No.: 15/911,796

(22) Filed: Mar. 5, 2018

(65) Prior Publication Data

US 2018/0325529 A1  Nov. 15, 2018

Related U.S. Application Data

(63) Continuation of application No. 14/490,079, filed on Sep. 18, 2014, now Pat. No. 9,907,559, which is a continuation of application No. 12/387,828, filed on May 8, 2009, now Pat. No. 8,870,873.

(51) Int. Cl.
*A61B 17/16* (2006.01)

(52) U.S. Cl.
CPC ........ *A61B 17/1631* (2013.01); *A61B 17/162* (2013.01); *A61B 17/1617* (2013.01); *A61B 17/1679* (2013.01); *A61B 17/1688* (2013.01)

(58) Field of Classification Search
CPC ............ A61B 17/1615; A61B 17/1617; A61B 17/162; A61B 17/1631; A61B 17/1633; A61B 17/1642; A61B 17/1662; A61B 17/1679; A61B 17/1688; B23B 45/005
USPC ....................................................... 408/127
See application file for complete search history.

(56) References Cited

U.S. PATENT DOCUMENTS

| | | |
|---|---|---|
| 1,630,239 A | 5/1927 | Binkley et al. |
| 2,725,495 A | 11/1955 | Rively |
| 3,867,943 A | 2/1975 | Nordin |
| 4,234,277 A * | 11/1980 | Benson ............... B23B 31/1071 279/75 |
| 4,265,231 A | 5/1981 | Scheller, Jr. et al. |
| 4,541,423 A | 9/1985 | Barber |
| 4,686,982 A | 8/1987 | Nash |
| 4,728,231 A | 3/1988 | Kunimori et al. |
| 4,811,736 A | 3/1989 | Griggs et al. |
| 5,242,461 A * | 9/1993 | Kortenbach ... A61B 17/320725 606/159 |
| 5,271,697 A | 12/1993 | Johnson et al. |
| 5,330,480 A * | 7/1994 | Meloul ............... A61B 17/1617 606/80 |
| 5,358,509 A | 10/1994 | Fine et al. |
| 5,437,630 A | 8/1995 | Daniel et al. |
| 5,478,093 A | 12/1995 | Eibl et al. |

(Continued)

*Primary Examiner* — Amy R Sipp
(74) *Attorney, Agent, or Firm* — Menuier Carlin & Curfman LLC

(57) ABSTRACT

A burr attachment designed for use with a curved burr attachment or other chuck attachments that includes a tube with a wire shaft supported therein and a coil spring surrounding said wire shaft and having each of the coils touch the outer periphery surface of the wire shaft and the inner peripheral surface of said tube to enhance cooling of said outer periphery of said tube from the heat generated by said wire shaft and attenuate vibrations while allowing said burr attachment to be bent without kinking.

21 Claims, 4 Drawing Sheets

(56) References Cited

U.S. PATENT DOCUMENTS

| | | |
|---|---|---|
| 5,499,984 A | 3/1996 | Steiner et al. |
| 5,505,737 A | 4/1996 | Gosselin et al. |
| 5,507,769 A | 4/1996 | Marin et al. |
| 5,741,263 A | 4/1998 | Umber et al. |
| 5,928,241 A | 1/1999 | Menut et al. |
| 5,895,179 A | 4/1999 | Gschwend et al. |
| 6,267,679 B1 | 7/2001 | Romano |
| 6,287,114 B1 | 9/2001 | Meller et al. |
| 7,066,940 B2 | 6/2006 | Riedel et al. |
| 7,488,322 B2 | 2/2009 | Brunnett et al. |
| 7,604,636 B1 | 10/2009 | Walters et al. |
| 8,273,097 B2 | 9/2012 | Malla et al. |
| 8,608,766 B2 | 12/2013 | Malla et al. |
| 8,870,873 B2 | 10/2014 | Del Rio et al. |
| 8,939,979 B2 | 1/2015 | Del Rio et al. |
| 2002/0009341 A1 | 1/2002 | Vasudeva |
| 2002/0038129 A1 | 3/2002 | Peters et al. |
| 2002/0071728 A1 | 6/2002 | Keefe et al. |
| 2002/0151902 A1 | 10/2002 | Riedel et al. |
| 2004/0194790 A1 | 10/2004 | Laufer et al. |
| 2005/0177168 A1* | 8/2005 | Brunnett ............ A61B 17/1624 606/80 |
| 2006/0229624 A1 | 10/2006 | May et al. |
| 2006/0241630 A1 | 10/2006 | Brunnett et al. |
| 2007/0088354 A1 | 4/2007 | Sugita |
| 2007/0100334 A1 | 5/2007 | McFarlin et al. |
| 2007/0100336 A1 | 5/2007 | McFarlin et al. |
| 2008/0249481 A1 | 10/2008 | Crainich et al. |
| 2008/0306334 A1 | 12/2008 | Okada |
| 2009/0131940 A1 | 5/2009 | Brunnett et al. |
| 2010/0063524 A1 | 3/2010 | McCombs |

\* cited by examiner

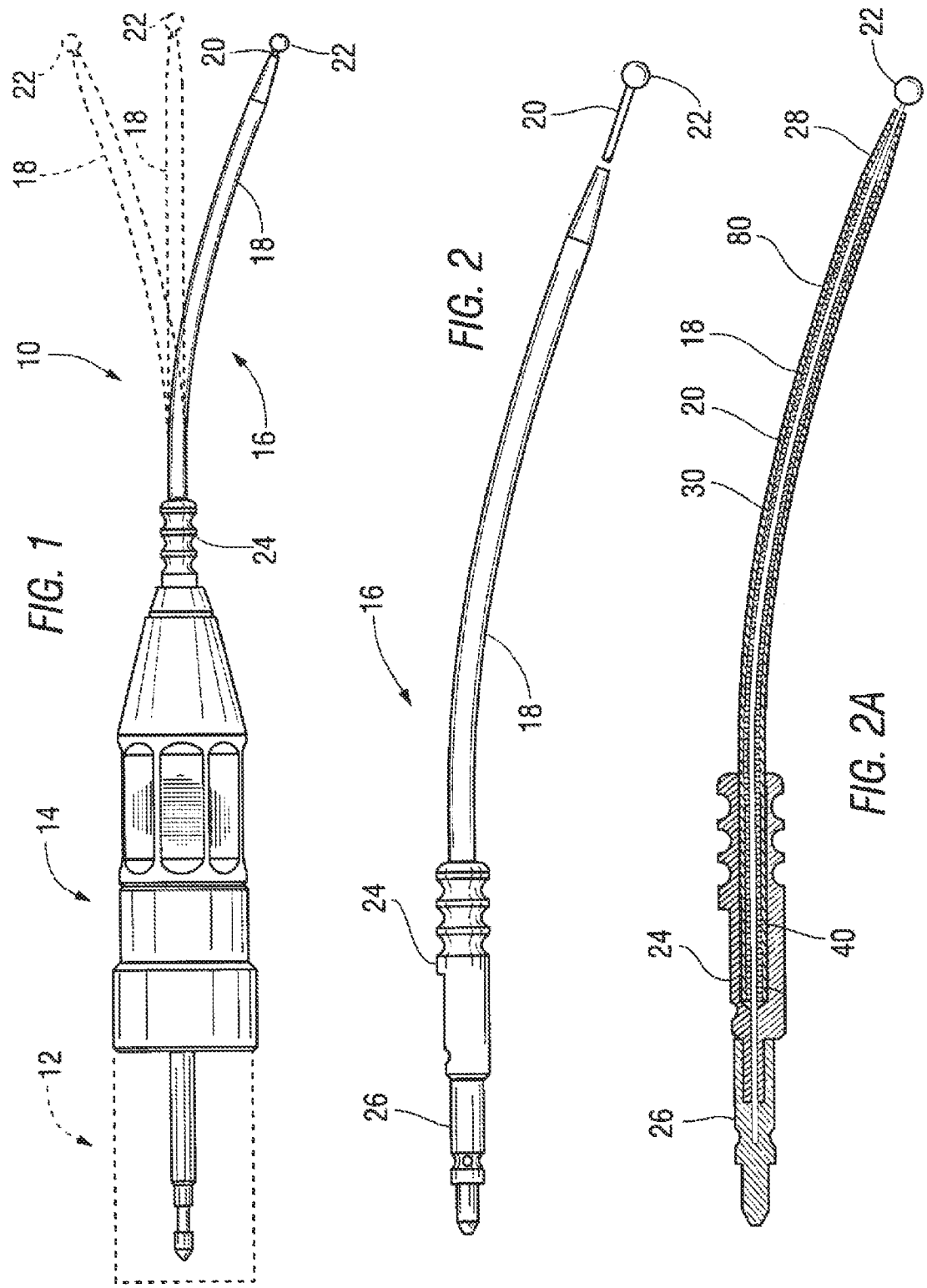

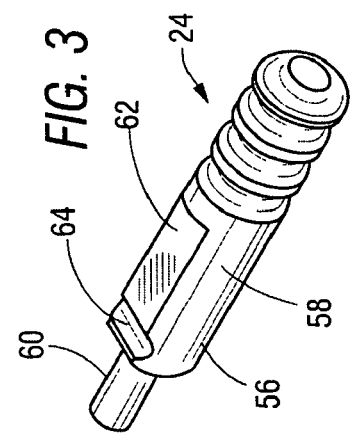
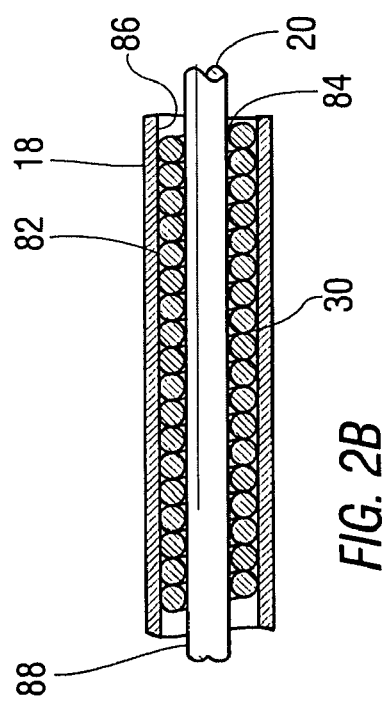
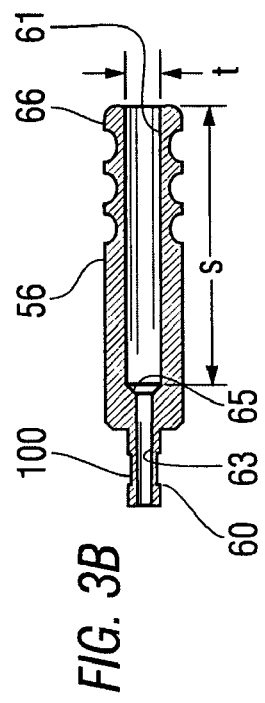
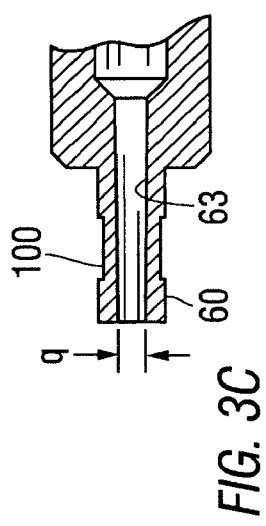
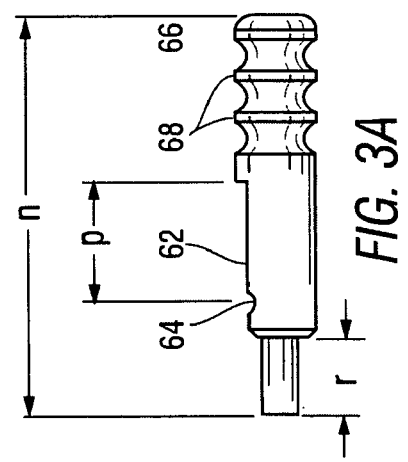

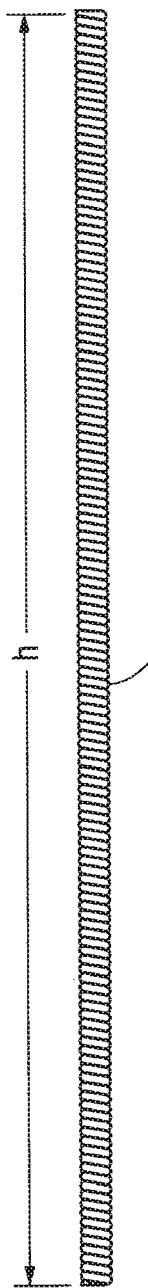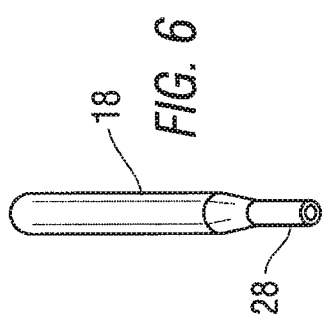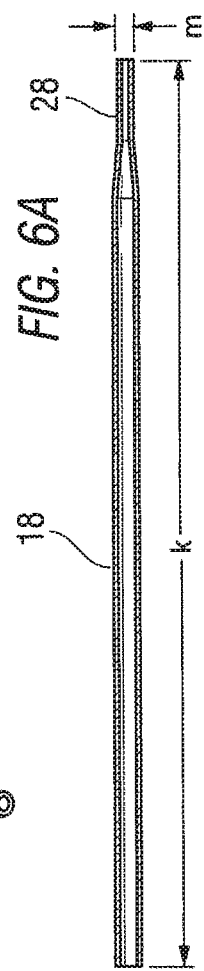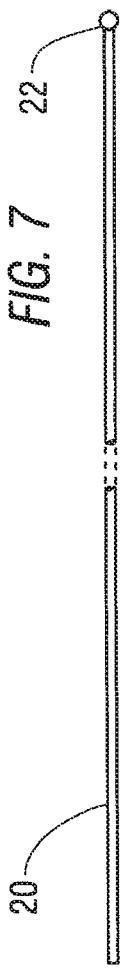

DISPOSABLE BURR ATTACHMENT

RELATED APPLICATIONS

This application claims priority to U.S. patent application Ser. No. 14/490,079, filed Sep. 18, 2014, entitled "DISPOSABLE BURR ATTACHMENT," which is a continuation of U.S. patent application Ser. No. 12/387,828, filed May 8, 2009, entitled "DISPOSABLE BURR ATTACHMENT" (issued as U.S. Pat. No. 8,870,873), the disclosures of which are incorporated herein by reference in its entirety. This invention relates to U.S. patent application Ser. No. 12/387,838, filed on May 8, 2009, "SURGICAL DRILL WITH CURVED BURR ATTACHMENT AND METHOD" (issued as U.S. Pat. No. 8,939,979), incorporated herein by reference in its entirety.

FEDERALLY SPONSORED RESEARCH OR DEVELOPMENT

Not applicable

TECHNICAL FIELD

This invention relates to a surgical cutting instrument (Curved Burr Attachment) and particularly to a portable and disposable burr attachment capable of use with the Curved Burr Attachment. The burr attachment of this invention has the ability to utilize different sized ball cutters primarily used for cutting bone and being capable of changing the angle of the attachment to different angles to fit into minute curved portions of the anatomy, as for example, the middle ear, although this surgical drill can be utilized for other surgical procedures.

BACKGROUND OF THE INVENTION

This invention is particularly efficacious because it is disposable and bendable without kinking and is characterized as being easily fitted into and removable from the adapter of a Curved Burr Attachment and that it is cost effective. What is meant by disposable in the context of this patent application is that the attachment, namely, the burr and its supporting structure (burr attachment) are detachable from the drill motor and the adapter and can be discarded. In the prior art, for example, the burr and its extensions are made integral with the adapter (sometimes referred to as the clutch or clutching mechanism) so that in order to make the burr disposable, the adapter, being attached thereto, is, of necessity, also disposable. It is readily understood that this is a less desirable scenario because it is less cost effective.

A good example of the differences between a more cost effective disposable component and a less cost effective disposable component is a comparison with the present invention and the instruments disclosed in the US Publication No. 2005/0177168 invented by Brunett, et al and entitled HIGH SPEED SURGICAL CUTTING INSTRUMENT (which is incorporated in its entirety herein by reference). In the present invention the comparable medical instrument is comprised of a motor, an adapter and the Curved Burr Attachment which is essentially the same elements of the instrument disclosed in the Publication, although the terminology is different. The elements in the instrument disclosed in the Publication, supra, that compares to the Curved Burr Attachment is the wire and the cutter extending at the end of the wire and its support structure, the chuck mechanism and the motor. Since the wire/cutter and support mechanism also includes an integral chuck mechanism (comparable to the adapter of the present invention) that serves to connect to the motor, the disposable portion includes the wire/cutter and its support mechanism, as well as the clutch mechanism. In contrast, the present invention merely disposes the burr attachment of the Curved Burr Attachment instrument and hence, the remaining portion of the instrument, namely, the adapter (the more expensive portions of the tool), are re-usable. What the industry needs and desires is a tool, of this type, which is extremely small, (ball cutters range in 0.5 mm-2 mm) which includes a disposable burr that is substantially inexpensive and hence, cost effective.

In addition to the ability to bend the burr attachment at-will and the burr attachment being disposable in a cost effective manner, the particular manner in which lubrication is applied to the burr is unique. In the present invention the wire-shaft of the burr is surrounded by a coil wire that extends to approximately from the proximate end to the distal end of the wire-shaft and is oriented in such a manner that the helix formed by the coil wire is in a upward direction so that by placing grease at the distal end, the rotation of the wire-shaft causes the grease to migrate from the distal end to the proximate end, namely, in the upward direction.

In addition to the lubrication feature and the bending without the kinking feature of the present invention, the coil wire which is fixed and non-rotatable, also serves another function, i.e. it dissipates heat. This is accomplished by judiciously locating the coil wire between the inner wall of the support sleeve or tube of the burr attachment and the wire-shaft such that the outer and inner edges of each coil touches both the side of the inner wall of the support sleeve and the outer periphery of the wire-shaft, respectively. This serves to conduct the heat away from the wire-shaft and from internally of the support sleeve. Distributing the heat dissipation load in this manner reduces the heat or slows down the heat at the cutter resulting in additional time that the Curved Burr Attachment can be in continuous use in a medical procedure. As one in this technology knows the heat generated by the cutter can adversely affect nerves and other portions of the anatomy. Further this arrangement attenuates vibrations created by the rotation of the wire shaft.

Another function of the coil wire is that it permits the bending of the burr attachment without causing kinking. In accordance with this invention, the burr attachment t may be bent at the factory and, at the option of the surgeon; it may be bent at-will.

SUMMARY OF THE INVENTION

An object of this invention is to provide an improved disposable burr attachment.

A feature of this invention is to provide a coil wire mounted in a support tube that surrounds the wire-shaft of the burr attachment such that it prevents kinking when the burr attachment is bent and it serves to provide heat transfer from the wire shaft to the inner diameter of the support tube surrounding the coil wire and provides a means for migrating grease from the distal end of the support tube upwardly toward the proximal end for lubricating the wire-shaft. This arrangement also attenuates vibrations created by the rotation of the coil wire.

Another feature of this invention is the inclusion of the proximal end support and the distal end support mounted on the end of the tube support that includes judicious dimensions that allow the attachment and the detachment of the burr attachment from the surgical instrument that provide means for rotating the wire shaft and locating the cutter in an exact and predetermined position.

Another feature of this invention is that it is designed to be disposable after a single use and is capable of use with a surgical drill that rotates at 80,000 revolutions per minute or higher.

The foregoing and other features of the present invention will become more apparent from the following description and accompanying drawings.

BRIEF DESCRIPTION OF THE DRAWINGS

FIG. 1 is a view in elevation and phantom illustrating a Curved Burr Attachment including the burr attachment of this invention attached thereto and illustrating the various positions that the instrument can be bent into;

FIG. 2 is a side elevation view of the burr attachment of the present invention;

FIG. 2A is a sectional view in elevation of the burr attachment depicted in FIG. 2.

FIG. 2B is a fragmentary enlarged view of a portion of FIG. 2A depicting the relationship of the wire shaft, the tube support and the coil wire of the present invention;

FIG. 3 is a perspective view of the distal end support of the present invention;

FIG. 3A is a side view in elevation illustrating the distal end support of the unit depicted in FIG. 3;

FIG. 3B is a sectional view of the distal end support depicted in FIG. 3;

FIG. 3C is an enlarged partial view of the distal end support including an annular groove formed on the peripheral surface of the smaller end portion formed in accordance with this invention;

FIG. 5 is an enlarged view in elevation illustrating the coil wire of this invention;

FIG. 6 is a perspective view illustrating the tube support tube for the burr attachment;

FIG. 6A is a sectional view of the support tube depicted in FIG. 6; and

FIG. 7 is a view in elevation of the wire shaft and cutter of this invention.

DETAILED DESCRIPTION OF THE INVENTION

Figure 4A:
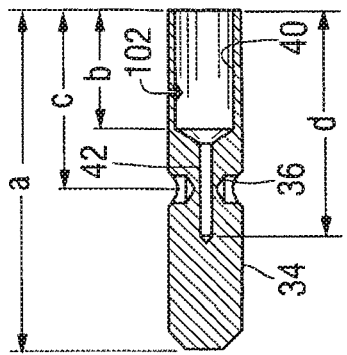
FIG. 4A is a sectional view of the proximal end support depicted in FIG. 4.

It will be noted that in the description of the elements of this invention as shown in each of the Figs. in this patent application may be out of proportion with respect to the overall picture of the inventive unit. As for example, some of the elements are shown in a small size and some of the elements are shown in an enlarged size. The purpose, obviously, is to more clearly define the invention and better describe the function of each of the elements. It is to be understood by those skilled in this art that the drawings are not manufacturing drawings, but are drawings used to illustrate the invention and to teach the concept and the workings thereof. Moreover, while the burr attachment of this invention is disclosed as being capable of use in a particular adapter, it is to be understood that other adapters can be used without departing from the scope of this invention and that this invention, amongst other things, teaches the concept of making the burr attachment, per se, disposable and bendable without incurring kinks.

As best seen in FIGS. 1 and 2, this invention is capable of use with a high speed (80,000 Io RPM-90,000 RPM) surgical instrument that is particularly efficacious for operating on small bones as for example, those found in the ear, nose and throat area, although not restricted thereto and generally illustrated as reference numeral 10 comprising a motor 12 (shown in phantom), an adapter 14 and the burr attachment 16 with the capability of being bent as shown in phantom and the burr attachment being disposable as will be described in detail herein below. While the particular motor used to rotate the drilling burr is of no moment, the X-Max® series or the E-Max® series, pneumatic and electric motors, respectively, are contemplated for use with this invention and are commercially available from the assignee of this invention, namely, The Anspach Effort, Inc of Palm Beach Gardens, Fla. 33410.

The adapter 14, while not a part of this invention, is described in the aforementioned patent application bearing Ser. No. 12/387,838 and for further details reference should be made to this document. Suffice it to say that the adapter is removably coupled to the motor and the burr attachment is removably coupled to the adapter for imparting rotary motion to the cutter that is attached to the wire shaft of the burr attachment.

The invention is best described by referring to all of the Figs wherein the medical instrument sometimes referred to as the Curved Burr Attachment generally indicated by reference numeral 10 comprising the motor 12 (shown in phantom, the adapter 14 and the burr attachment 16, which is the subject matter of this invention. The burr attachment 16 is removably coupled to the adapter 14 as described in the aforementioned application bearing Ser. No. 12/387,828 and comprises a tube support 18, a wire shaft 20 and cutter 22, a distal end support 24, a proximal end support 26 (see FIGS. 2 & 3), coil wire 30, and nose cap 28. The cutter 22 may be a spherical ball with a diamond coating or with cut-in flutes. These devices are well known and for this particular medical instrument these cutters are particularly small, say from 0.5 mm to 2 mm.

All the elements of the burr attachment are made from a surgical steel or other suitable material where the hardness and tensile strength of the wire shaft 20 and attached cutter 22, the tube 18, proximal end support 26, distal end support 24 and nose cap 28 are higher than the hardness and tensile strength of the coil wire 30. (Unlike a spring, the coil wire 30 does not exhibit any springlike characteristics and has no spring rate) These parameters are selected to assure that the burr attachment is sufficiently rigid to support the high rotational speed, yet the wire coil 30 is sufficiently malleable so that the burr attachment can be hand bent without incurring any kinking.

Figure 4C:
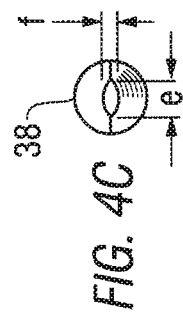
FIG. 4C is an end view of the unit depicted in FIG. 4.
Figure 4D:
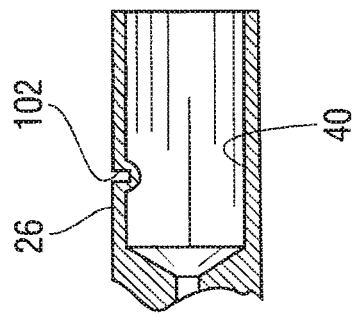
FIG. 4D is an enlarged partial view of the proximal end support illustrating An indent to be formed on the peripheral surface of the smaller end portion in accordance with this invention.
Figure 4:
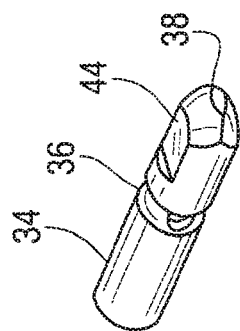
FIG. 4 is a perspective view of the proximal end support of this invention.
Figure 4B:
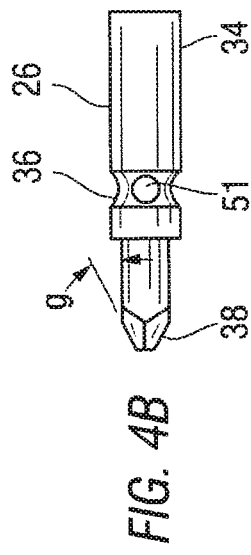
FIG. 4B is a side elevation view of the proximal end support depicted in FIG. 4.

As alluded to in the above paragraphs, the burr attachment 16 is disposable. Hence, this invention assures that the burr attachment 16 is both easily inserted into and easily removed from the adapter. To this end the distal end support 24 and proximal end support 26 are judiciously dimensioned. As best seen in FIGS. 3, 3A 3B, 4A, 4B and 4C, the proximal end support 26 includes a generally cylindrical shaped main body 34, an annular groove 36 disposed intermediate the ends thereof, a tip portion 38, a flat portion 44 formed on the periphery of the main body 34 and adjacent to the tip portion 38, large diameter recess 40 formed on one end remote from the tip portion 38 and a smaller diameter bore 42 extending axially from the large diameter recess 40. Preferably the tip portion 38 is asymmetrically shaped so that the tip is formed in a shape of an ellipse as shown in FIG. 4C. The larger diameter recess 40 serves to receive the proximal end of the distal end support 24 as will be described in more detail herein below. The smaller diameter bore 42 serves to receive the proximal end of the wire shaft 20 which is united to the proximal end support 26, say, by swaging, shrink fitting or the like. In this particular embodiment, the holes 51 serve to receive a tool (not shown) used to swage the main body 34 to wire shaft 20 to form an integral unit so that the wire shaft 20 rotates with the proximal end support 26 for powering the cutter 22. The annular groove 36 serves to cooperate with the adapter such that it couples the burr attachment so that the proximal end support 26 and wire shaft 20 are rotated. The pertinent dimensions of the proximal end support 26 are as follows in inches:

a=0.450; b 0.160; c=0.235; d=0.300; e=0.051; f=0.20; i=0.020 and the tip angle g=30°

The distal end support 24, as best seen in FIGS. 3, 3A and 3B, comprises a generally cylindrical main body 56 including a larger diameter portion 58, a smaller diameter portion 60, a flat portion 62 formed on the periphery of the main body 56 intermediate the ends thereof, a slot 64 formed on the periphery of the main body 56 adjacent to a flat portion 62 formed on the periphery of the main body 56, a larger diameter recess 61, a smaller diameter bore 63 and a grip portion 66 formed on the end of the main body 56 remote from the smaller diameter portion 60. The slot 64 cooperates with the adapter such that it locates the cutter relative to the tip of the adapter and the distal end support is held fixed relative to the adapter. The grip portion 66 in this embodiment is formed by axially spaced annular ribs but other known configurations, like knurling, can be employed. The pertinent dimensions of the distal end support 24 are substantially as follows in inches:

n=0.785; p=0.276; r=0.150; s=0.550; t=0.0725 and q=0.026

As noted in FIG. 2 the peripheral end support 26 is fitted into the distal end support 24 such that the smaller diameter 60 fits into the slot 40 and the proximal end of the tube support 18 and coil wire 30 fits into the larger diameter recess 61, which define a seat 65 therefore. The diameter of the bore 63 (0.026) is larger than the diameter of the of the wire shaft 20 (0.020) such that it is capable of freely rotate therein and since the wire shaft 20 is locked into the peripheral end support 26 it will rotate when the adapter rotates the peripheral end support 26. The wire shaft 20 and cutter 22 are shown in FIG. 7.

As noted from FIG. 2A the coil wire 30 is mounted in the seat 80 defined by the proximal end of the nose cap 28 and the seat 65 defined by the proximal end of the recess 61 and is held in place between these seats. When the coil wire 30 is installed into the tube 18 each end thereof bears against the spring seat 65 and the spring seat 80 formed when the nose cap 28 is inserted, such that the nose cap 28 will hold the coil wire 30 in place. This assures that coil wire 30, surrounding the rotating wire shaft 20, remains fixed. Hence, when the wire shaft is rotating, randomly, each of the coils of the coil wire will touch the inner surface of the tube 18 and outer periphery of the coil wire 30. An enlarged view of the coil wire is shown in FIG. 5 where the substantial value of h=2.240. A view of the tube support 18 is disclosed in FIGS. 6 and 6A where the substantial values of k=2.650 and m=0.042.

It will also be noted and in accordance with this invention that the helix orientation of the coils of coil wire 30 are in a direction as seen in FIG. 28 are from right to left or looking from the right hand end of FIG. 28 they are in a clockwise direction. The direction of the helix serves to flow grease in the upward direction toward the proximal end. Because of the orientation of the coils, grease inserted at the distal end of the burr attachment unit in a clearance between the wire shaft 20 and inner diameter of the nose cap 22 into the tube 18 so that when the wire shaft 20 rotates this motion forces the grease toward the proximal end of the burr attachment which lubricates the entire the wire shaft 20.

It will also be noted and in accordance with this invention, as evidenced in FIG. 2B, that the peripheral top and bottom surfaces 82 and 84 of each coil of coil wire 30 touch, by a point contact, the inner diameter surface 86 of tube support 18 and the outer surface 88 of wire shaft 20 and this connection serves to minimize the heat transfer through the coil wire 30 and tube 18. This minimizing of the heat transfer of wire shaft 20 serves to keep the outer tube 18 cooler than it would otherwise be without this feature. The importance of maintaining the outer surface of tube 18 cooler by virtue of this heat transfer feature of this invention results in enhancing the operational time of the Curved Burr Attachment. In addition, because of the location of the coil wire 30, namely, by the touching of the wire shaft 20 and of the inner surface of tube 18, vibration generated by the rotating wire shaft 20 of the Curved Burr Attachment is attenuated.

It will be appreciated that in certain operations, particularly affecting the ear, the surgeon may have to re-adjust the angle of the burr attachment. Since the coil wire 30 is mounted between tube 28 and wire shaft 20, the surgeon can bend the burr attachment to any desired angle to suit the particular operation being performed. Because of this design, the burr attachment 16 will not kink and will leave a smooth bend and yet the tube and wire shaft will provide sufficient rigidity to perform the rotation in a precise manner.

In some of the embodiments of this invention the diameter of cutter 22 is smaller than the diameter of the wire shaft 20 which could under certain circumstances cause a problem, as for example, in the insertion and removal of the burr attachment 16. To solve this problem the distal end support 24 includes the annular groove 100 formed on the smaller diameter portion 60. And a dimple or indent 102 is formed on the larger diameter portion 34 adjacent to the larger bore portion 40 of the proximal end support 26, obviating the possibility of the cutter 22 and wire shaft 20 from inadvertently falling out. Obviously, the dimple or indent 102 is formed after the proximal end support 26 and the distal end support 24 are assembled in the assembled burr attachment 16.

Although this invention has been shown and described with respect to detailed embodiments thereof, it will be appreciated and understood by those skilled in the art that various changes in form and detail thereof may be made without departing from the spirit and scope of the disclosed invention.

We claim:
1. A burr attachment comprising:
a proximal support member capable of being inserted into a chuck driven by a motor for imparting rotary motion thereto, the proximal support member including:

a first flat formed adjacent a proximal end of the proximal support member for orienting and fixing the proximal support member within a chuck, and a second flat formed opposite a longitudinal axis of the proximal support member from the first flat, a first tapered surface extending between the first flat and an end surface of the proximal support member, the end surface defining a generally elliptical-shaped planar surface, a height of the elliptical-shaped planar surface, measured in a plane perpendicular to the first and second flats, is less than a corresponding height of the proximal support member measured in a plane perpendicular to the first and second flats between leading edges of each of the first and second tapered surfaces; and an elongated wire shaft is fixedly coupled to the proximal support member, the wire shaft including a distal end for coupling with a corresponding cutter.

2. The burr attachment of claim 1, wherein the proximal support member includes an annular groove extending around a periphery of the proximal support member, the annular groove formed intermediate the first flat and a distal end of the proximal support member.

3. The burr attachment of claim 2, wherein a center of the annular groove is located about 0.235 inches from the distal end of the proximal support member.

4. The burr attachment of claim 2, wherein the wire shaft is received within a central bore extending axially and partially within the proximal support member, wherein the wire shaft is fixedly coupled to the proximal support member at a location proximate a longitudinal position of the annular groove.

5. The burr attachment of claim 2, wherein the annular groove includes a hole extending into the proximal support member in a direction transverse to the longitudinal axis of the proximal support member, the hole sized and configured to receive a tool for coupling the proximal support member to the wire shaft.

6. The burr attachment of claim 5, wherein the wire shaft is coupled to the proximal support member by swaging.

7. The burr attachment of claim 5, wherein the wire shaft is received within a central bore provided in the proximal support member,
wherein the hole does not extend into the central bore.

8. The burr attachment of claim 1,
wherein a length of the second flat along the longitudinal axis of the proximal support member corresponds to a length of the first flat along the longitudinal axis of the proximal support member.

9. The burr attachment of claim 8, wherein the first and second flats each define a generally planar surface extending generally parallel to the longitudinal axis of the proximal support member,
wherein a height of the first flat, measured between the longitudinal axis and the planar surface of the first flat, corresponds to a second height of the second flat, measured between the longitudinal axis and the planar surface of the second flat.

10. The burr attachment of claim 8, wherein the proximal support member further includes a second tapered surface extending between the second flat and the end surface of the proximal support member.

11. The burr attachment of claim 10, wherein each of the first and second tapered surfaces extend at an angle of about 30-degrees with respect to the longitudinal axis of the proximal support member.

12. The burr attachment of claim 10,
wherein a width of the elliptical-shaped planar surface, measured in a plane parallel to the first and second flats, is less than a corresponding width of the proximal support member measured between the leading edges of the first and second tapered surfaces in a plane parallel to the first and second flats.

13. The burr attachment of claim 10, wherein the height of the elliptical-shaped planar surface, measured in the plane perpendicular to the first and second flats, is about 0.051 inches,
wherein a width of the elliptical-shaped planar surface, measured in a plane parallel to the first and second flats, is about 0.20 inches.

14. A burr attachment comprising:
an elongated wire shaft including a distal end for coupling with a corresponding cutter;
a proximal support member capable of being inserted into a chuck driven by a motor for imparting rotary motion thereto, the proximal support member fixedly coupled to the wire shaft for imparting rotary motion thereto; and
a distal support member received within a central bore extending in the proximal support member such that the distal support member is rotatable relative to the proximal support member, the distal support member including a reduced diameter portion formed at a proximal end thereof and a larger diameter portion formed at a distal end thereof, the larger diameter portion including a flat formed proximate the reduced diameter portion and a groove formed on the flat, the groove extending in a direction generally perpendicular with a longitudinal axis of the distal support member,
wherein the wire shaft extends through the distal support member and is fixedly coupled to the proximal support member such that the wire shaft is rotatable relative to the distal support member.

15. The burr attachment of claim 14, wherein said distal support member is about 0.785 inches long,
wherein the reduced diameter portion is about 0.150 inches long,
wherein a center of the groove is located about 0.276 inches from a proximal end of end of the flat.

16. The burr attachment of claim 14, wherein the distal support member includes:
the reduced diameter portion sized and configured to be received within the central bore of the proximal support member;
an annular groove formed on the reduced diameter portion, the groove having a first edge adjacent a proximal end of the reduced diameter portion and a second edge adjacent a distal end of the reduced diameter portion,
wherein a width of the annular groove is greater than a distance between the proximal end of the distal support member and the first edge of the annular groove.

17. The burr attachment of claim 14, wherein the central bore extending in the proximal support member includes:
a large diameter portion formed at a distal end of the proximal support member, where the distal support member is received within the large diameter portion of the central bore, and
a small diameter portion extending axially from the large diameter portion towards a proximal end of the proximal support member, where the wire shaft is received within and fixedly coupled to the proximal support member at the small diameter portion.

18. The burr attachment of claim 17,
wherein a length of the large diameter portion of the bore extending in the proximal support member corresponds with a length of the reduced diameter portion of the distal support member such that an entire length of the reduced diameter portion is received within the large diameter portion of the bore extending in the proximal support member.

19. The burr attachment of claim 17, wherein the proximal support member includes a recess formed on an outer surface proximate the large diameter portion of the central bore and a corresponding detent projecting into the large diameter portion of the central bore, the recess and the detent being axially aligned in a direction transverse to a longitudinal axis of the proximal support member,
wherein engagement between the detent and the distal support member retains the distal support member within the central bore of the proximal support member.

20. A burr attachment comprising:
an elongated wire shaft including a distal end for coupling with a corresponding cutter;
a proximal support member capable of being inserted into a chuck driven by a motor for imparting rotary motion thereto, the proximal support member fixedly coupled to the wire shaft for imparting rotary motion thereto; and
a distal support member received within a central bore extending in the proximal support member such that the distal support member is rotatable relative to the proximal support member, the distal support member including:
  a reduced diameter portion formed at a proximal end thereof and a larger diameter portion formed at a distal end thereof, the reduced diameter portion sized and configured to be received within the central bore of the proximal support member, and
  an annular groove formed on the reduced diameter portion, the groove having a first edge adjacent a proximal end of the reduced diameter portion and a second edge adjacent a distal end of the reduced diameter portion, where a width of the annular groove is greater than a distance between the proximal end of the distal support member and the first edge of the annular groove,
wherein the wire shaft extends through the distal support member and is fixedly coupled to the proximal support member such that the wire shaft is rotatable relative to the distal support member.

21. A burr attachment comprising:
an elongated wire shaft including a distal end for coupling with a corresponding cutter;
a proximal support member capable of being inserted into a chuck driven by a motor for imparting rotary motion thereto, the proximal support member fixedly coupled to the wire shaft for imparting rotary motion thereto, the proximal support member including:
  a recess formed on an outer surface proximate of a central bore, and
  a corresponding detent projecting into the central bore, the recess and the detent being axially aligned in a direction transverse to a longitudinal axis of the proximal support member; and
a distal support member received within the central bore extending in the proximal support member such that the distal support member is rotatable relative to the proximal support member,
wherein the wire shaft extends through the distal support member and is fixedly coupled to the proximal support member such that the wire shaft is rotatable relative to the distal support member,
wherein engagement between the detent and the distal support member retains the distal support member within the central bore of the proximal support member.

* * * * *